United States Patent
Li et al.

(10) Patent No.: US 9,872,851 B2
(45) Date of Patent: *Jan. 23, 2018

(54) METHODS OF TREATING PORTAL HYPERTENSION

(71) Applicant: The Charlotte-Mecklenburg Hospital Authority, Charlotte, NC (US)

(72) Inventors: Ting Li, Charlotte, NC (US); Laura Schrum, Charlotte, NC (US); Jonel Trebicka, Bonn (DE)

(73) Assignee: THE CHARLOTTE-MECKLENBURG HOSPITAL AUTHORITY, Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/651,418

(22) PCT Filed: Dec. 12, 2013

(86) PCT No.: PCT/US2013/074833
§ 371 (c)(1),
(2) Date: Jun. 11, 2015

(87) PCT Pub. No.: WO2014/093726
PCT Pub. Date: Jun. 19, 2014

(65) Prior Publication Data
US 2015/0313871 A1    Nov. 5, 2015

Related U.S. Application Data (60) Provisional application No. 61/736,307, filed on Dec. 12, 2012, provisional application No. 61/736,850, filed on Dec. 13, 2012, provisional application No. 61/787,395, filed on Mar. 15, 2013.

(51) Int. Cl.
| | |
|---|---|
| *A61K 31/381* | (2006.01) |
| *A61K 45/06* | (2006.01) |
| *A61K 31/4025* | (2006.01) |
| *A61K 31/7105* | (2006.01) |
| *A61K 47/54* | (2017.01) |
| *A61K 47/64* | (2017.01) |
| *A61K 47/66* | (2017.01) |

(52) U.S. Cl.
CPC ........ *A61K 31/381* (2013.01); *A61K 31/4025* (2013.01); *A61K 31/7105* (2013.01); *A61K 45/06* (2013.01); *A61K 47/549* (2017.08); *A61K 47/643* (2017.08); *A61K 47/66* (2017.08)

(58) Field of Classification Search
CPC .............. A61K 2300/00; A61K 31/381; A61K 31/4025; A61K 31/7105; A61K 45/06; A61K 47/48092; A61K 47/48284; A61K 47/48346

See application file for complete search history.

(56) References Cited

U.S. PATENT DOCUMENTS

2013/0053429 A1* 2/2013 Schrum ................ A61K 31/713
514/44 A

FOREIGN PATENT DOCUMENTS

WO    2011022619 A1    2/2011

OTHER PUBLICATIONS

Bataller et al. (Journal of Clinical Investigation 2005;115(2):209-218).*
Marjolijn et al. (Pharm. Res. 2011;28:2045-2054).*
Lakner et al. (Hepatology Jul. 2012;56(1):300-310).*
Saito Circulation;127(1):Nov. 2012 21:104-114; 32 pages.*
Chew et al. (Diabetes Care, 2008;31(8):1502-1509) 8 pages.*
Reynaert et al. (Gut 2002;(50):571-581).*
Sprague et al. (Biochem Pharmacol. 2009;78(6):539-552).*
Migita et al. (FEBS Letters, 2004;561:69-74).*
Garcia-Tsao et al. (Am J Gastroenterol 2009,104:1802-1829).*
Notification of Transmittal of the International Search Report and the Written Opinion for corresponding PCT Application No. PCT/US2013/074833, dated Feb. 19, 2014, 13 pages.
Laura A. Solt et al., "Regulation of circadian behaviour and metabolism by synthetic REV-ERB agonists", Nature 11030, vol. 485, No. 7396, Mar. 29, 2012, pp. 62-68.
Naresh Kumar et al., "Regulation of Adipogenesis by Natural and Synthetic REV-ERB Ligands", Endocrinology, vol. 151, No. 7, Jul. 1, 2010, 18 pages.
T. Li et al., "Functional Role of REV-ERB in Modulation of Hepatic Stellate Cell Transdifferentiation", Journal of Hepatology, vol. 56, 2012, p. S152.

* cited by examiner

*Primary Examiner* — Ernst V Arnold
(74) *Attorney, Agent, or Firm* — Erin C. Wills; John P. Zimmer; Smith Moore Leatherwood LLP (57) ABSTRACT

The present invention provides methods for treating or preventing portal hypertension comprising administering to a patient in need of such treatment or prevention at least one Rev-erb modulating agent (REMA) in an amount effective to treat or prevent said portal hypertension. The REMA can be SR6452 or a related compound, such as SR9009 or SR9011. The amount of the REMA administered can comprises a quantity sufficient to modulate Rev-erbα expression, activity, and/or subcellular location and/or to inhibit or reverse hepatic stellate cell (HSC) activation and contractility.

17 Claims, 6 Drawing Sheets

METHODS OF TREATING PORTAL HYPERTENSION

The present application claims priority to U.S. Provisional Application No. 61/787,395, filed Mar. 15, 2013, U.S. Provisional Application No. 61/736,850, filed Dec. 13, 2012, and U.S. Provisional Application No. 61/736,307, filed Dec. 12, 2012, all of which are incorporated herein by reference in their entirety.

FIELD OF THE INVENTION

The present invention is directed to compositions and associated methods for the treatment, prevention, and/or amelioration of portal hypertension. In particular, certain embodiments of the present invention relate to methods of using a Rev-erb-modulating agent (REMA) for the treatment of portal hypertension.

BACKGROUND OF THE INVENTION

Portal hypertension is a condition in which high blood pressure is present in the portal vein and its tributaries. It is often defined as a portal pressure gradient (the difference in pressure between the portal vein and the hepatic veins) of 5 mmHg or greater. Portal hypertension has profound clinical consequences, some of which can be associated with substantial morbidity and mortality. In most instances, an increase in intrahepatic resistance to blood flow is an early and critical component to portal hypertension. Recent evidence links perisinusoidal stellate cells (also known as Ito cells or lipocytes), which are analogous to tissue pericytes or vascular smooth muscle cells, to a role in portal hypertension via their capacity to regulate blood flow within the liver by contraction and constriction of sinusoids.

In an injured liver, hepatic stellate cells (HSCs) undergo a striking functional transition termed "activation". Activation of HSCs in response to liver injury is a critical event in wound healing. For instance, HSC activation is a pivotal event in initiation and progression of hepatic fibrosis. HSC activation is characterized by cellular transdifferentiation from a vitamin A-storing quiescent adipocyte-like phenotype to a highly contractile and secretory myofibroblast phenotype. Dysregulation of transdifferentiation results in disruption of normal liver architecture, leading to negative pathophysiological consequences including portal hypertension, fibrosis and ultimately cirrhosis.

A critical feature of activation is the acquisition by HSCs of smooth muscle proteins, including smooth muscle alpha actin ($\alpha$SMA) and myosin. As noted above, this transition is associated with an enhanced contractile phenotype; as a result of activation, HSC contractility is greatest in the injured liver. The increased contractility facilitates an increase in vascular resistance to the portal blood flow. Recent approaches to counterbalancing this increased portal vascular resistance due to the increased contractility of HSCs have focused on using vasodilating drugs (e.g., nitric oxide, organic nitrates, adrenolytics, calcium channel blockers, etc.). Such approaches, however, do not adequately treat, prevent, and/or ameliorate portal hypertension itself.

Accordingly there is a need for portal hypertension therapies designed to impede or halt further development of portal hypertension and/or reverse portal hypertension.

BRIEF SUMMARY OF THE INVENTION

One or more embodiments of the present invention may address one or more of the aforementioned problems. Certain embodiments according to the present invention provide methods for treating, preventing, ameliorating and/or delaying onset of portal hypertension in a mammal suffering from portal hypertension or symptoms associated with portal hypertension or in a mammal at an increased risk of developing portal hypertension (e.g., based on diagnosis of other conditions that are known to lead to portal hypertension). The portal hypertension can be a symptom of one or more diseases and/or conditions that lead to liver cirrhosis, such as viral hepatitis, autoimmune hepatitis, drug induced liver injury (DILI), alcoholism, a metabolic disorder, or parasitic infection. In certain embodiments, the portal hypertension is a symptom of a disease and/or condition other than non-alcoholic fatty liver disease (NAFLD), non-alcoholic steatohepatitis (NASH), obesity, a metabolic disease, and autoimmune hepatitis.

In certain embodiments, the methods comprise administering a composition comprising a therapeutically effective amount of one or more Rev-erb-modulating agents (REMA) to a mammal. The REMA can at least partially modulate (e.g., upregulate or downregulate) the expression, activity, or subcellular localization of at least one Rev-erb (e.g., Rev-erb$\alpha$ and/or Rev-erb$\beta$) in at least a portion of the mammal's hepatic stellate cells (HSCs). In certain preferred embodiments, the composition includes an amount of at least one REMA sufficient to modulate (e.g., upregulate or downregulate) at least one of Rev-erb$\alpha$ (and/or Rev-erb$\beta$) expression, activity, or localization and reduce HSC activation.

The REMA can comprise a variety of forms, e.g., synthetic/natural ligand, enzyme, protein, nucleic acid, etc. In certain embodiments, the methods comprise administering a composition comprising a therapeutically effective amount of SR6452 (i.e., 1,1-Dimethylethyl-N-[(4-chlorophenyl)methyl]-N-[(5-nitro-2-thienyl)methyl])glycinate) or a related compound to the mammal in need. In certain embodiments, the REMA is a compound selected from the group consisting of SR9009 and SR9011. The REMA can be linked to a carrier/targeting moiety, such as mannose-6-phosphate modified human serum albumin. The carrier/targeting moiety can, for example, increase the serum half-life of the REMA and/or selectively deliver the REMA to HSCs.

In certain embodiments, the composition comprising a REMA can be administered along with at least one non-REMA therapeutic agent. The non-REMA therapeutic agent can be administered as part of the same composition or administered separately. In certain embodiments, the non-REMA therapeutic agent is selected from the group consisting of anti-viral agents, anti-fibrotic agents, an immunomodulatory agent, a cellular agent (e.g., stem cells) and/or agents that suppress HSC activation. In certain embodiments, the non-REMA therapeutic agent is a miRNA, e.g., miR-19b.

In another aspect, the present invention provides a wide range of pharmaceutical compositions that can be administered to a mammal, such as a human, to treat, prevent, ameliorate and/or delay the onset of portal hypertension in the mammal. In accordance with certain embodiments, the pharmaceutical compositions can comprise a therapeutically effective amount of one or more REMAs (optionally linked to a carrier/targeting moiety) and at least one pharmaceutically acceptable carrier. In other embodiments, the pharmaceutical composition can comprise a mixture of one or more REMAs and one or more non-REMA therapeutic agents (e.g., an anti-viral agent, an anti-fibrotic agent, an immunomodulatory agent, a cellular agent such as stem cells, or an agent that suppresses HSC activation). The pharmaceutical compositions can be formulated for administration to a mammal (e.g., a human) by various routes.

BRIEF DESCRIPTION OF THE DRAWINGS

Having described the invention in general terms, reference will now be made to the accompanying drawings.

FIGS. 1A-1C illustrate modulation of Rev-erbα expression during HSC transdifferentiation. Primary rat HSCs were isolated and culture-activated through day (d) 20. Freshly isolated cells were considered quiescent (dQ). Cells were harvested for total RNA (FIGS. 1A and 1B) or protein (FIG. 1C), and qRT-PCR or Western blots performed to detect Rev-erbα mRNA or protein expression, respectively. Pai-1 (FIG. 1B) and αSMA (FIG. 1C) were used as positive controls for HSC culture-activation.

FIG. 2A shows the results from freshly isolated primary rat HSCs that were culture-activated through day 4 in the presence of MDIR (a pro-adipogenic mixture) or embedded in matrigel. FIG. 2A also shows results from human LX-2 cells that were embedded in matrigel for 72 hrs. FIG. 2B shows the results from primary HSCs that were treated with pro-fibrogenic factor TGFβ (5 ng/ml) or myosin inhibitors blebbistatin (Bleb) or BDM (2,3-Butanedione monoxime) for 48 hrs. Cells were harvested for protein and Western blots performed to detect Rev-erbα.

FIGS. 3A-B illustrate how modulation of Rev-erbα activity can regulate adipogenesis. Primary HSCs were culture-activated for 5 days (A) or 15 days (B). Cells were treated with vehicle, DMSO (open bar), or Rev-erb agonist SR6452 (10 mM, solid bar). FIG. 3A provides a graph summarizing the amount of PPARγ, SREBP1, and Lep mRNA detected after 5 days of culture. On day 15, cells were stained with Oil Red O as an indicator of adipogenesis, and the results are shown in FIG. 3B.

FIG. 5C shows results in which HSCs (day 9) were treated with DMSO or SR6452 for 72 hrs and immunocytochemistry was performed for αSMA (red fluorescence) and 4',6-diamidino-2-phenylindole (DAPI) (blue fluorescence). FIG. 5D shows HSCs (day 5) that were embedded in a collagen gel and treated as indicated for 48 hrs. Gels were released from plastic surface and contraction monitored after 72 hrs. Materials used were DMSO, vehicle control; SR6452, Rev-erb agonist; and BDM (2,3-Butanedione monoxime), myosin inhibitor.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Increased synthesis and deposition of type I collagen by activated HSCs is ultimately a major cause of organ dysfunction as a result of liver injury. In the normal/healthy liver, HSCs reside in a quiescent state, functioning to store vitamin A, modulating microcirculation, and regulating extracellular matrix (ECM) production. Following injury, HSCs transdifferentiate into an activated myofibroblast-like cell characterized by loss of vitamin A droplets, changes in cytoskeletal protein expression, including smooth muscle α-actin (αSMA), and hyper-contractility leading to decreased sinusoidal blood flow. Initiation of HSC activation is concomitant with the presence of several inflammatory and immunomodulatory molecules. The increased contractility associated with activation of HSCs leads to an undesirable increase in vascular resistance to the portal blood flow, which can ultimately lead to portal hypertension.

In one aspect, the present invention provides methods for treating, preventing, reversing, ameliorating and/or delaying the onset of portal hypertension in a mammal suffering from portal hypertension or symptoms associated with portal hypertension or in a mammal at an increased risk of developing portal hypertension (e.g., based on diagnosis of other conditions that are known to lead to portal hypertension). Generally, portal hypertension is considered a symptom of another underlying condition or illness. Common conditions that give rise to portal hypertension include cirrhosis of the liver, which can be caused by chronic viral hepatitis (e.g., caused by HCV, HBV, etc.), autoimmune hepatitis, chronic alcoholism, drug induced liver injury (DILI) (e.g., caused by prescription drugs, non-prescription drugs, or toxins), non-alcoholic fatty liver disease (NAFLD), non-alcoholic steatohepatitis (NASH), bile duct disease, a genetic diseases (e.g., hemochromatosis, glycogen storage disease, alpha-1 antitrypsin deficiency, Wilson disease, cystic fibrosis, primary sclerosing cholanitis), malnutrition, cardiac problems, and parasitic infection (e.g., Schistosomiasis infection). In certain embodiments, the cause of the portal hypertension is a condition other than NAFLD, NASH, obesity, a metabolic disease and/or autoimmune hepatitis. In certain embodiments, the cause of the portal hypertension is DILI (e.g., caused by a drug overdose or a drug administered as part of a clinical trial).

In the liver, various fibrogenic mediators stimulate the activation and proliferation of collagen-producing cells, including hepatic stellate cells (HSCs). Without intending to be bound by theory, it is believed that such fibrogenic mediators influence the expression, activity and subcellular location of Rev-erbs, such as Rev-erbα and Rev-erbβ. For example, cytoplasmic Rev-erbs appears to be profibrotic, while nuclear Rev-erbs appears to help maintain the adipogenic or quiescent phenotype. At least some fibrogenic mediators appear to stabilize cytoplasmic Rev-erbα, thereby stimulating the activation of HSCs.

Accordingly, in certain embodiments of the present invention, the methods of the invention involve the treatment of cells (e.g., collagen-producing cells) or a mammal suffering from portal hypertension by administering a therapeutically effective amount of one or more Rev-erb-modulating agents (REMA). In preferred embodiments, the composition includes an amount of at least one REMA sufficient to modulate (e.g., upregulate or downregulate) the expression, activity, and/or subcellular localization of at least one of Rev-erb (e.g., Rev-erbα and/or Rev-erbβ). In certain embodiments, the composition modulates at least one Rev-erb (e.g., Rev-erbα and/or Rev-erbβ) by destabilizing cytoplasmic Rev-erb and stimulating nuclear localization, or vice versa. Modulation of the subcellular localization of Rev-erb isoforms (e.g., Rev-erbα and/or Rev-erbβ) according to certain embodiments of the present invention can beneficially impact HSCs. That is, the degree to which the HSCs are activated and/or the contractility of the HSCs can be beneficially reduced.

Rev-Erb Modulating Agents (REMAs)

Preferably, embodiments of the present invention utilize the administration of one or more REMAs to a mammal. In accordance with certain embodiments, the REMA is not particularly limited as long as the agent either directly or indirectly modulates (e.g., upregulates or downregulates) Rev-erbα expression, function, activity, and/or localization within HSCs. In certain embodiments, the REMA also modulates the expression, function, activity, and/or activity of at least one Rev-erb other than Rev-erbα (e.g., Rev-erbβ) within HSCs.

Rev-erbs are transcriptional repressors known to localize to the nucleus. As such, most studies have previously focused on its activity as a transcriptional factor. However, an increased cytoplasmic expression of Rev-erbα in activating or activated HSCs can also undesirably provide a contractile function. Accordingly, certain embodiments of the present invention can comprise directly or indirectly modulating Rev-erbα cytoplasmic expression to at least partially mitigate the contractile function associated with Rev-erbα cytoplasmic expression in HSCs.

Generally speaking, the term "REMA" as used herein, refer to compounds (e.g., small molecules, ligands, proteins, enzymes, antibodies, nucleic acids, etc.) that affect the activity of Rev-erbs in vivo and/or in vitro. REMAs can be agonists of Rev-erbs and can be compounds that exert their effect on Rev-erb activity via altering expression, via post-translational modifications, or by other means. Agonists of Rev-erbs can comprise molecules which, when bound to a Rev-erb, increase or prolong the activity of the Rev-erb (e.g., increase the nuclear localization and/or nuclear activity of Rev-erbα). Agonists of Rev-erbα according to certain embodiments of the present invention can include proteins, nucleic acids, carbohydrates, small molecules, or any other molecules which activate Rev-erbα. In certain embodiments, agonists of Rev-erbα also function as agonists of Rev-erbβ by increasing or prolonging the activity of Rev-erbβ (e.g., increasing the nuclear localization and/or nuclear activity of Rev-erbβ).

The term "modulate", as it appears herein, refers to a change in the activity or expression of a Rev-erb, such as Rev-erbα. For example, modulation may cause an increase or a decrease in protein activity, binding characteristics, or cellular localization, or any other biological, functional, or immunological properties of the Rev-erb.

In certain embodiments, the REMA can directly modulate Rev-erbα activity, expression, and/or subcellular localization in HSCs. In certain preferred embodiments, the REMA comprises a synthetic ligand that modulates Rev-erbα activity or expression. For instance, in certain embodiments, the REMA can comprise a synthetic agonist for Rev-erbα. Modulators of Rev-erb activity and/or expression have been disclosed, e.g., in WO 2013/033310, the contents of which are incorporated herein by reference. Additional modulators of Rev-erb activity can be identified by screening potential compounds, e.g., as described in Grant et al. (2010), ACS Chem. Biol. 5(10):925-32, the contents of which are incorporated herein by reference. Such potential compounds can include, for example, variants of any REMA compound specifically disclosed herein.

Exemplary synthetic agonists for Rev-erbs include 1,1-Dimethylethyl N-[(4-chlorophenyl)methyl]-N-[(5-nitro-2-thienyl)methyl])glycinate; N-Benzyl-N-(4-chlorobenzyl)-1-(5-nitrothiophen-2-yl)methanamine; N-Benzyl-N-(3,4-dichlorobenzyl)-1-(5-nitrothiophen-2-yl)methanamine; 2-((4-chlorobenzyl)((5-nitrothiophen-2-yl)methyl)amino)-N,N-dimethylacetamide; or combinations thereof. Other exemplary synthetic agonists for Rev-erbs include SR9009 and SR9011, which are described in WO 2013/033310 and are structurally related to the foregoing synthetic agonists. See, e.g., FIG. 1.

Certain embodiments of the present invention utilize the administration of synthetic Rev-erb agonist 1,1-Dimethylethyl-N-[(4-chlorophenyl)methyl]-N-[(5-nitro-2-thienyl)methyl])glycinate ($EC_{50}$=250 nM) or a salt thereof, which is known as SR6452 or GSK4112 and is commercially available from Sigma Aldrich (USA). 1,1-Dimethylethyl-N-[(4-chlorophenyl)methyl]-N-[(5-nitro-2-thienyl)methyl])glycinate will hereinafter be referred to as "SR6452". Rev-erb agonist SR6452 enhances recruitment of nuclear receptor co-repressor (NCoR) peptide to Rev-erbα. The structure of SR6452 is as follows:

In certain embodiments, the REMA can comprise N-Benzyl-N-(4-chlorobenzyl)-1-(5-nitrothiophen-2-yl)methanamine. The structure of N-Benzyl-N-(4-chlorobenzyl)-1-(5-nitrothiophen-2-yl)methanamine is as follows:

In certain embodiments, the REMA can comprise N-Benzyl-N-(3,4-dichlorobenzyl)-1-(5-nitrothiophen-2-yl)methanamine. The structure of N-Benzyl-N-(3,4-dichlorobenzyl)-1-(5-nitrothiophen-2-yl)methanamine is as follows:

In certain embodiments, the REMA can comprise 2-((4-chlorobenzyl)((5-nitrothiophen-2-yl)methyl)amino)-N,N-dimethylacetamide. The structure of 2-((4-chlorobenzyl)((5-nitrothiophen-2-yl)methyl)amino)-N,N-dimethylacetamide is as follows:

In certain embodiments, the REMA is a compound related to SR6452, such as SR9009 or SR9011. See, e.g., WO 2013/033310.

In accordance with certain embodiments of the present invention, the REMA can comprise a natural molecule (e.g., Heme modulators). For instance, a natural REMA can include enzymes, antibodies, proteins, nucleic acids, carbohydrates, small molecules, or combination thereof including upstream regulators (both known such as GSK3β and/or novel).

To improve efficacy and/or reduce side effects, the REMA can be linked to another moiety that functions as a carrier and/or targeting moiety. Preferably, the other moiety selectively targets HSCs. Suitable targeting moieties include, e.g., mannose-6-phosphate modified human serum albumin. See, e.g., van Beuge et al. (2013), PLOS ONE 8(2): e56442, the contents of which are incorporated herein by reference. The carrier/targeting moiety can, in some embodiments, increase the serum half-life of the REMA. In other embodiments, the carrier/targeting moiety increases the serum half-life of the REMA and selectively targets HSCs.

According to certain embodiments of the present invention, REMAs can indirectly modulate Rev-erbα activity or expression. In such embodiments, the REMA preferably targets or interacts with a component of the HSC upstream to Rev-erbα expression or a component that regulates nuclear transport of Rev-erbα. This component, for instance, can then function to modulate Rev-erbα expression or activity. Accordingly, the REMA effectively modulates Rev-erbα activity or expression indirectly through interaction with the upstream component of the HSC that subsequently affects the activity or expression of Rev-erbα due to the initial interaction with the REMA. In certain such embodiments, the REMA can comprise enzymes, antibodies, proteins, nucleic acids, carbohydrates, small molecules, or combinations thereof. The component of the HSC upstream to Rev-erbα expression can comprise, for example, an enzyme, antibody, protein, nucleic acid, carbohydrate, or combinations thereof including upstream regulators (known regulators, such as GSK3β, and/or novel regulators).

Rev-Erb

Rev-erb proteins are members of the nuclear receptor family of intracellular transcription factors. There are two forms of the receptor, alpha (α) and beta (β), each encoded by a separate gene (NR1D1 and NR1D2 respectively).

Rev-erbα, also known as NR1D1 (nuclear receptor subfamily 1, group D, member 1) is a transcriptional repressor. Rev-erbα is highly expressed in the liver, skeletal muscle, adipose tissue, and the brain, in mammals, participating in the development and circadian regulation of these tissues. Preitner N, et al., (2002). "The orphan nuclear receptor Rev-erbα controls circadian transcription within the positive limb of the mammalian circadian oscillator". Cell 110 (2): 251-60. doi:10.1016/S0092-8674(02)00825-5. PMID 12150932; Triqueneaux G, et al, (2004). "The orphan receptor Rev-erbα gene is a target of the circadian clock pacemaker". J. Mol. Endocrinol. 33 (3): 585-608. doi:10.1677/jme.1.01554. PMID 15591021. Gibbs, et al., 2009 Circadian Timing in the Lung; a Specific Role for Bronchiolar Epithelial Cells, Endocrinology 2009. 150:268-276. doi 10.1210/en.2008-0638. Rev-erbα regulates gene transcription by directly binding to target response elements (RevREs), comprises an A/T-rich flank followed by AGGTCA. Rev-erbα mediates repression by recruiting the corepressor N-CoR, which then activates the histone deacetylase (HDAC) 3.

Therapeutically Effective Amount

In accordance with certain embodiments of the present invention, a therapeutically effective amount of a REMA can generally comprise an amount sufficient to achieve its intended purpose. More specifically, a therapeutically effective amount can comprise an amount effective to prevent development of portal hypertension or alleviate the existing symptoms, or revert activated HSCs back to a quiescent state in the subject being treated. A therapeutically effective amount can vary based on a range of factors (e.g., route of administration, patient's age, patient's weight, severity of disorder, etc.) and determination thereof is well within the capability of those skilled in the art.

For instance, a therapeutically effective amount of a REMA can be estimated initially from cell culture assays. For example, a dose can be formulated in animal models to achieve a circulating concentration range that includes the IC50 (the dose where 50% of the cells show the desired effects) as determined in cell culture. Such information can be used to more accurately determine useful doses in mammals (e.g., humans).

A therapeutically effective amount of a REMA can also refer to that amount of the compound that results in amelioration of symptoms or a prolongation of survival in a patient. Toxicity and therapeutic efficacy of a REMA can be determined by standard pharmaceutical procedures in cell cultures or experimental animals (e.g., for determining the LD50—the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosages or amounts for use in mammals (e.g., humans). The dosage or amount of SR6452 preferably lies within a range of circulating concentrations that include the ED50 with little or no toxicity. The dosage or amount may vary within this range depending upon the dosage form employed and the route of administration utilized. The exact formulation, route of administration and dosage can be chosen by the individual physician in view of the patient's condition. Dosage amount and interval may be adjusted individually to provide plasma levels of the active moiety which are sufficient to maintain the desired effects.

In cases of local administration or selective uptake, the effective local concentration of the REMA may not be related to plasma concentration.

The amount of REMA-containing composition administered can, of course, be dependent upon several factors including the subject being treated, on the subject's weight, the severity of the affliction, the manner of administration and the judgment of the prescribing physician.

In certain embodiments of the present invention, a REMA can be administered to a mammal having portal hypertension, exhibiting symptoms of portal hypertension, or determined to be at risk of developing portal hypertension in an amount sufficient to modulate (e.g., upregulate or downregulate) Rev-erb (e.g., Rev-erbα) expression, activity, and/or subcellular location, impede activation of HSCs, and/or revert activated HSCs into a quiescent state. In accordance with certain embodiments, Rev-erb (e.g., Rev-erbα) expression and/or activity can be modulated (e.g., upregulated or downregulated) by at least 1%, 5%, 10%, 15%, 20%, 25%, 30%, 35%, 40%, 45%, 50%, 55%, 60%, 65%, 70%, 75%, 80%, 85%, 90%, 95%, or more. For instance, Rev-erb expression and/or activity can be modulated (e.g., upregulated or downregulated) from at least any of the following: 1%, 5%, 10%, 15%, 20%, 25%, 30%, 35%, 40%, 45%, 50%, 55%, 60%, 65%, 70%, 75%, 80%, 85%, 90%, 95%, and/or at most about any of the following 5%, 10%, 15%, 20%, 25%, 30%, 35%, 40%, 45%, 50%, 55%, 60%, 65%, 70%, 75%, 80%, 85%, 90%, 95%, 100% (e.g., 5-100%, 10-90%, 20-80%, etc.). In other embodiments, Rev-erb (e.g., Rev-erbα) subcellular localization can be modulated (e.g., shifted to the nucleus) by at least 1%, 5%, 10%, 15%, 20%, 25%, 30%, 35%, 40%, 45%, 50%, 55%, 60%, 65%, 70%, 75%, 80%, 85%, 90%, 95%, or more. For instance, Rev-erb (e.g., Rev-erbα) subcellular localization can be modulated (e.g., shifted to the nucleus) such that the amount of Rev-erb in a particular location (e.g., the nucleus) is from at least any of the following: 30%, 35%, 40%, 45%, 50%, 55%, 60%, 65%, 70%, 75%, 80%, 85%, 90%, 95%, to at most about any of the following 80%, 85%, 90%, 95%, 100% (e.g., 30-100%, 40-90%, 50-80%, etc.).

In certain embodiments, the methods can comprise the administration of a therapeutically effective amount of a REMA, in which the amount of the REMA comprises an amount sufficient to halt activation of hepatic stellate cells concomitantly with modulation (e.g., upregulation or downregulation) of Rev-erbα expression, activity, and/or subcellular location. For instance, the rate at with HSCs are activated begins to reduce until no noticeable further activation of additional HSCs is realized. In this regard, these embodiments can provide a means to effectively impede or stop the further restriction (e.g., increased restriction with time) of portal blood flow so as to prevent compounding current complications.

In certain preferred embodiments, the methods can comprise the administration of a therapeutically effective amount of a REMA, in which the amount of the REMA comprises an amount sufficient to revert at least a portion of any activated HSCs into a quiescent phenotype concomitantly with modulation (e.g., upregulation or downregulation) of Rev-erbα expression, activity, and/or subcellular location. In such embodiments, the degree of portal vascular restriction can be reduced to beneficially reduce the restriction of portal blood flow. That is, when activated HSCs revert back into a quiescent phenotype (associated with healthy or normal HSCs) their degree of contractility reduces (e.g., the HSCs "relax" from a contracted state). This "relaxation" of the HSCs can beneficially reduce the "choking-like" restriction on portal vein blood flow, and decrease portal pressure preferably below 12 mmHg, as a cut-off for the variceal bleeding. However, in clinical use a decrease of 20% in portal pressure is most welcome since studies show thereby a significant decrease of bleeding. In certain embodiments of the present invention, the percentage reduction in portal pressure, due to certain methods of the present invention, can comprise a reduction of at least any of 5%, 10%, 15%, 20%, 25%, 30%, 35%, 40%, 45%, and 50%; and/or at most any of 30%, 35%, 40%, 45%, 50%, 55%, 60%, 65%, 70%, and 75% (e.g., percentage reduction in portal pressure from 5%-30%, 15%-40%, 10%-20%, etc.).

In certain embodiments, for instance, the HSCs of a mammal exhibit an initial degree of contractility prior to administration of a REMA. The initial degree of contractility can be evaluated, for example, based on a measurement of the portal pressure gradient as is known in the art. After administration of a composition comprising a therapeutically effective amount of the REMA, the HSCs of the mammal exhibit a second degree of contractility that is less than the initial degree of contractility. Again, the second degree of contractility can be evaluated, for example, based on a measurement of the portal pressure gradient as is known in the art. In certain preferred embodiments, the second degree of contractility subsequent to administration of the REMA is sufficiently reduced in comparison to the initial degree of contractility such that at least a portion of the mammals liver sinusoids are at least partially relaxed.

The relaxed state of contractility realized after treatment according to certain embodiments of the present invention can be exhibited or realized at least once from 15 minutes to 24 hours from the time of administration (e.g., intravenously, orally, or in cell-culture). For instance, the relaxed state of contractility realized after treatment according to certain embodiments of the present invention can be exhibited or realized at least after any of 0.25, 0.5, 1.0, 2, 4, 6, 10, 12, and 18 hours after administration; and/or at most any of 8, 12, 15, 18, 24, 36, and 48 hours after administration (e.g., between 0.25-24 hours, 1-18 hours, 4-8 hours, etc. from the time of administration). In certain embodiments, the portal pressure gradient can be monitored continuously or in intervals to facilitate identification of a need for a second treatment, variance in dosage amount, and/or development of a treatment schedule for days or weeks.

In certain embodiments, the mammal (e.g., human) being treated has been diagnosed as having portal hypertension. In other embodiments, however, the mammal (e.g., human) being treated may not technically have portal hypertension but may be exhibiting symptoms similar to or associated with portal hypertension. In certain embodiments, the mammal (e.g., human) being treated may be identified as being at risk of developing portal hypertension in view of diagnosis of conditions known to ultimately lead to development of portal hypertension (e.g., liver fibrosis, liver cirrhosis, viral liver infections, chemically-induced liver damage, etc.). In such embodiments, the administration of a REMA in accordance with certain embodiments of the present invention can beneficially facilitate or prevent development of portal hypertension.

Methods according to certain embodiments of the present invention can comprise administering a therapeutically effective amount of a REMA to a patient in which the patient also suffers from at least one of liver fibrosis, hepatic cirrhosis, acute alcoholic hepatitis, schistosomiasis, primary biliary cirrhosis, idiopathic portal hypertension, acute and fulminant hepatitis, congenital hepatic fibrosis, peliosis hepatitis, veno-occlusive disease, Budd-Chiari syndrome, vitamin A toxicity, Sclerosing cholangitis, Hepatitis B, Hepatitis C, non-alcoholic steatophepatitis (NASH), alcoholic liver disease (ALD), a metabolic liver disease, Wilson's disease, and hemochromatosis.

In certain embodiments of the present invention, the methods of treatment can comprise a combination therapy including a treatment method as described herein in combination with another treatment, such as a tradition method of treating portal hypertension, including, e.g., diet, medications, endoscopic therapy, surgery, or radiology. In certain embodiments, methods of treatment can comprise administering a therapeutically effective amount of one or more REMAs to a patient concomitantly, serially, or in an alternating fashion (e.g., variable or fixed dosing regimens) with another therapeutic agent. The other therapeutic agent can be one that is designed to treat the underlying cause of the hepatic fibrosis, such as an anti-viral agent (e.g., an anti-HCV or anti-HBV agent). For example, the anti-viral agent can be ribavirin, peginterferon alpha-2a, boceprevir, telaprevir, raltegravir, entecavir, sofosbuvir, mericitabine, setrobuvir, declatasvir, ledipasvir, asunaprevir, faldaprevir, simeprevir, danoprevir, sovaprevir, miravirsen, VX-135, VX-222, ABT-267, ABT-333, BI207127, GS-5816, GS-9451, GS-9669, GSK2336805, ACH-3102, TMC647055, ACH-3102, MK-5172, MK-8742, IDX719, or any combination thereof. Alternatively, the other therapeutic agent can be one that is designed to treat hepatic fibrosis and/or inhibit activation of HSCs, such as miR-19b (see, e.g., US Application 2013/0053429, the content of which is incorporated herein by reference), an angiotensin II receptor antagonist (e.g., irbesartan, losartan, or candesartan), oltipraz, or GS-6624. Other therapeutic agents suitable for combination therapy include traditional medicaments for treating portal hypertension (e.g., vasodilators, nitric oxide, organic nitrates, adrenolytics, calcium channel blockers, and beta blockers).

As discussed throughout, the methods according to embodiments of the present invention generally comprise administering a composition comprising at least one REMA. In another aspect, as such, the present invention also provides a wide range of pharmaceutical compositions that can be administered to a mammal by various routes to treat, prevent, and/or ameliorate portal hypertension in the mammal. In accordance with certain embodiments, the pharmaceutical compositions can comprise a therapeutically effective amount of a synthetic compound (e.g., SR6452, SR9009, SR9011) and at least one pharmaceutically acceptable carrier or excipient.

In accordance with certain embodiments of the present invention, the pharmaceutical compositions can comprise SR6452 in combination with a wide variety of pharmaceutically acceptable carriers or excipients. The particular carriers or excipients can be varied depending on various factors including route of administration, presence or absence of a carrier/targeting moiety, desired delivery system (e.g., sustained release, timed-released, immediate release, selective release, etc.). For example, the composition can be made to suit the desired mode of administration. Pharmaceutically acceptable carriers can be determined, in part, by the particular composition being administered, as well as by the particular method used to administer the composition. Accordingly, there is a wide variety of suitable formulation recipes of pharmaceutical compositions containing one or more REMAs. For example, the pharmaceutical carrier may comprise a virus, a liposome (e.g., cationic lipids mixed with a REMA to form liposomes carrying the REMA), or a polymer (e.g., cationic polymers such as DEAE-dextran or polyethylenimine in which the REMA complexes with the polycation and the complex is taken up by the cell via endocytosis).

The administration of a pharmaceutical composition comprising a REMA may be carried out by known methods, wherein a desired molecule is introduced into a desired target cell in vitro or in vivo. In general, methods of administering small molecule agonists are well known in the art. REMA compositions in accordance with certain embodiments of the present invention can be administered by a number of routes including, but not limited to: oral, intravenous, intraperitoneal, intraarterial, intramuscular, transdermal, subcutaneous, topical, sublingual, or rectal means. Alternatively, the REMA can be administered using a cellular vehicle, such as cells "loaded" with the REMA ex vivo.

Administration of the formulations described herein may be accomplished by any acceptable method which allows a REMA to reach its target. Any acceptable method known to one of ordinary skill in the art may be used to administer a formulation to the subject. The administration may be localized (i.e., to a particular region, physiological system, tissue, organ, or cell type) or systemic, depending on the condition being treated. In certain embodiments, the targeted tissue comprises a HSC.

Injections can be, for example, intravenous, intradermal, subcutaneous, intramuscular, or intraperitoneal. In certain embodiments, the injections can be given at multiple locations if desired. In certain embodiments, the compositions can be delivered by implantation. Implantation can include inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. In certain embodiments, the compositions can be delivered by inhalation. Inhalation can include administering the composition with an aerosol in an inhaler, either alone or attached to a carrier that can be absorbed. For systemic administration, it may be preferred that the composition is encapsulated in liposomes.

Preferably, the REMA delivery systems are provided in a manner which enables tissue-specific uptake of the REMA. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

In certain embodiments according to embodiments of the present invention, a nucleic acid encoding a REMA molecule can be provided on a vector. Such vectors can include a sequence encoding a particular REMA of choice and in vivo expression elements. Vectors can include, but are not limited to, plasmids, cosmids, phagemids, viruses, other vehicles derived from viral or bacterial sources that have been manipulated by the insertion or incorporation of the nucleic acid sequences for producing the desired REMA, and free nucleic acid fragments which can be attached to these nucleic acid sequences. Viral and retroviral vectors are a preferred type of vector according to certain embodiments and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV40-type viruses; polyoma viruses; Epstein-Ban viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Genetically altered retroviral expression vectors have general utility for the high-efficiency transduction of nucleic acids in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Cliffton, N.J. (1991).

In certain embodiments, a therapeutically effective amount of one or more REMAs can be delivered to a mammal via a nanoparticle-based drug delivery system. Nanoparticle-based drug delivery systems can have considerable potential for treatment of portal hypertension. For instance, nanoparticles used as carriers for REMAs can provide the benefits of high stability, high carrier capacity, feasibility of incorporation of both hydrophilic and hydrophobic substances, and feasibility of variable routes of administration, including oral application and inhalation. In certain embodiments, the nanoparticles can also be designed to allow controlled (sustained) release of the REMA from the matrix. The aforementioned properties of nanoparticles, according to certain embodiments of the present invention, can provide improvement of bioavailability and/or reduction of the dosing frequency. Nanoparticles for the purpose of REMA delivery can be defined as submicron (<1 μm) colloidal particles. The colloidal particles can include monolithic nanoparticles (nanospheres) in which the REMA is adsorbed, dissolved, or dispersed throughout the matrix and nanocapsules in which the REMA is confined to an aqueous or oily core surrounded by a shell-like wall. Alternatively, the REMA can be covalently attached to the surface or into the matrix. Nanoparticles, according to certain embodiments of the present invention, can be made from biocompatible and biodegradable materials such as polymers, either natural (e.g., gelatin, albumin) or synthetic (e.g., polylactides, polyalkylcyanoacrylates), or solid lipids. In the body of the mammal being treated, the REMA loaded in nanoparticles can be released from the matrix by a variety of mechanisms including, for example, diffusion, swelling, erosion, degradation, or combinations thereof.

In one embodiment, the composition comprising the REMA can be perfused directly through the targeted tissue, such as the liver. For example, the composition containing the REMA can be perfused directly through a body organ (e.g., liver), without introducing the REMA into the body's general circulation, removing them from the organ with effluent blood and transporting the contaminated blood to an extracorporeal circuit where the blood is treated to remove the contamination, and returning the treated blood to the body. In some embodiments, such a process may help prevent undesirable levels of the REMA from entering the body's general circulation while delivering effective doses to the HSCs. Methods of perfusing active agents through a body organ, such as the liver, are described in greater detail in U.S. Pat. No. 5,069,662, the contents of which are incorporated by reference in their entirety.

In certain embodiments, the compositions can be delivered using a bioerodible implant by way of diffusion or by degradation of a polymeric matrix. In certain embodiments, the administration of the compositions may be designed so as to result in sequential exposures to the REMA over a certain time period, for example, hours, days, weeks, months or years. This may be accomplished, for example, by repeated administrations or by a sustained or controlled release delivery system in which REMA is delivered over a prolonged period without repeated administrations. Administration of the compositions using such a delivery system may be, for example, by oral dosage forms (e.g., tablet, capsule, etc.), bolus injections, transdermal patches or subcutaneous implants. Maintaining a substantially constant concentration of the REMA may be preferred in some cases.

Other suitable delivery systems include, but are not limited to, time-release, delayed release, sustained release, or controlled release delivery systems (e.g., tablets, capsules, etc.). Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which a REMA is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133, 974 and 5,407,686). The compositions may be as, for example, microspheres, hydrogels, polymeric reservoirs, cholesterol matrices, or polymeric systems. In certain embodiments, the system may allow sustained or controlled release of the composition to occur, for example, through control of the diffusion or erosion/degradation rate of the formulation containing the REMA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose can be determined by the efficacy of the particular formulation, and the activity, stability or serum half-life of the REMA employed and the condition of the patient, as well as the body weight or surface area of the patient to be treated. The size of the dose can also be determined by the existence, nature, and extent of any adverse side-effects that accompany the administration of a particular composition in a particular patient.

Therapeutic compositions comprising a REMA can optionally be tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the REMA at various concentrations, e.g., as applied to the mass and overall health of the patient. Administration can be accomplished via single or divided doses.

Compositions according to certain embodiments described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers.

EXAMPLES

Example 1: Involvement of Rev-Erbα in HSC Transdifferentiation

A series of experiments were conducted to determine the functional role of Rev-erbα in HSC transdifferentiation. In these experiments, culture-activated primary rat HSCs and human LX-2 cells were used. To determine the effect of Rev-erbα on HSC transdifferentiation and contraction, cells were treated with a specific synthetic modulator, SR6452 (10 µM). mRNA and protein expression were determined by qRT-PCR and Western blot, respectively. Changes in cellular morphology, Rev-erbα expression/localization and αSMA expression were observed by confocal microscopy. Additionally, cell contractility was assessed.

I. Materials and Methods
Primary Cell Isolation and Culture
Primary rat HSCs were isolated by pronase/collagenase perfusion digestion followed by density gradient centrifugation with Optiprep. Media was replaced every other day to replenish Rev-erb modulator SR6452, which was present at a 10 µM concentration. Cells were treated with MDIR mixture (IBMX, dexamethasone, insulin, rosiglitazone), TGFβ, or DMSO (vehicle). Some experiments were performed with the human HSC cell line, LX-2.
Quantitative Real-Time PCR (qRT-PCR)
mRNA expression was normalized to 18S rRNA.
Immunocytochemistry
Prior to transfection, culture-activated HSCs (for varying days of activation) were seeded onto glass coverslips. Cells were fixed with 4% paraformaldehyde and stained with anti-αSMA antibody, a marker of HSC activation. Cells were imaged using a Zeiss confocal microscope. The fluorescence indicates Rev-erbα or αSMA expression.
Cell Contraction Assay
Primary rat HSCs (day 9, 2-5×10$^6$ cells/ml) were embedded in a collagen lattice per manufacturer's instructions. Cells were treated with synthetic Rev-erbα ligand SR6452. Collagen gel size change was imaged using a BioSpectrum Imaging System.
Statistical Analysis
Data are presented as mean±SEM as determined from at least two independent experiments.

Figure 1A:
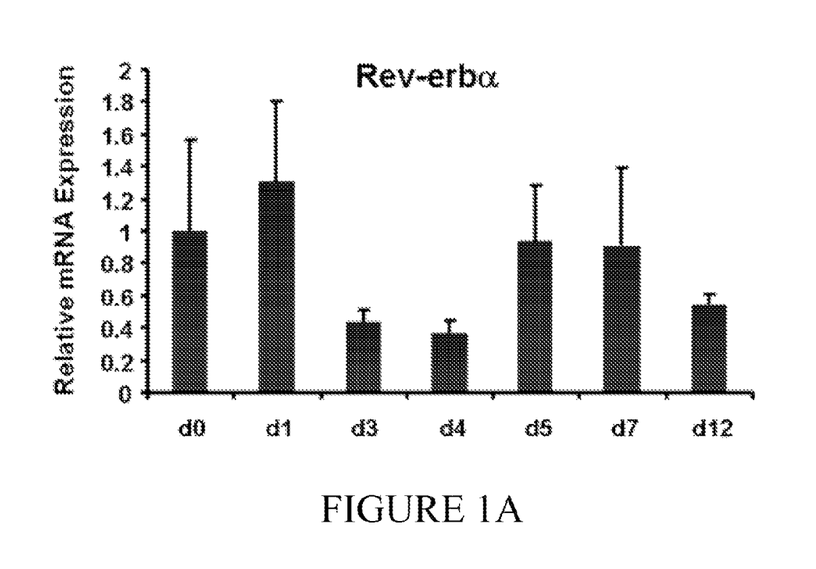
Figure 1B:
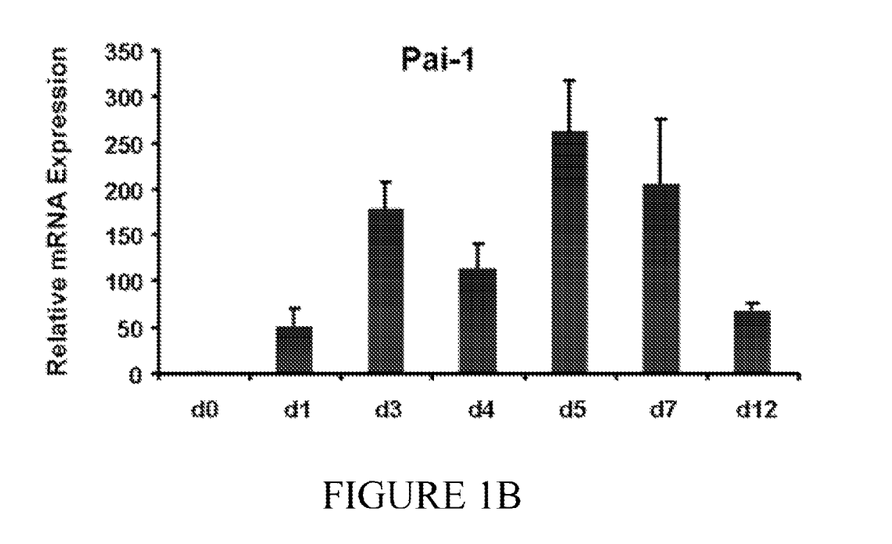
Figure 1C:
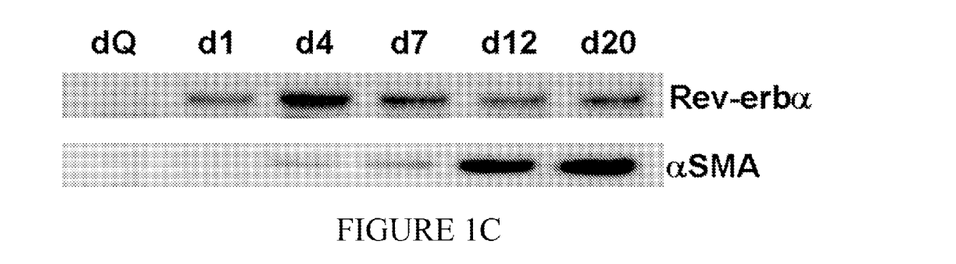

II. Results
FIGS. 1A-1B show that Rev-erbα expression is modulated during HSC transdifferentiation. Primary rat HSCs were isolated and culture-activated through day (d) 20. Freshly isolated cells were considered quiescent (dQ). Cells were harvested for total RNA (FIGS. 1A and 1B) or protein (FIG. 1C) and qRT-PCR or Western blots were performed to detect Rev-erbα expression. Pai-1 (FIG. 1B) and αSMA (FIG. 1C) were used as positive controls for HSC culture-activation.

Figure 2A:
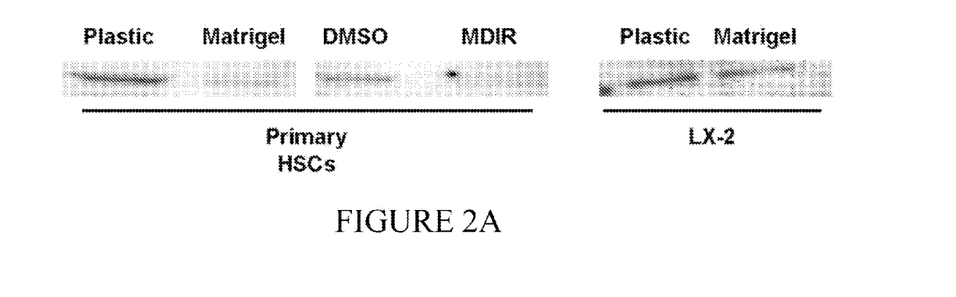
FIGS. 2A-B illustrate the regulation of Rev-erbα expression by pro- and anti-fibrogenic factors.
Figure 2B:
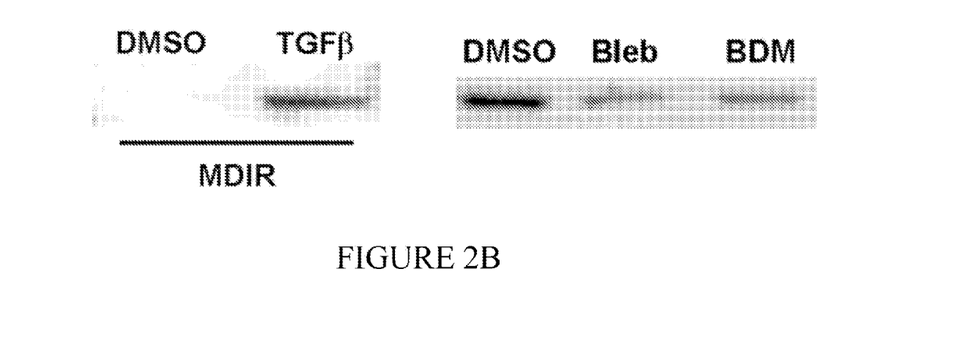

FIGS. 2A-B show that regulation of Rev-erbα expression can be controlled by both pro- and anti-fibrogenic factors. FIG. 2A shows results from freshly isolated primary rat HSCs that were culture-activated through day 4 in the presence of MDIR, a pro-adipogenic mixture, or embedded in matrigel. FIG. 2A also shows results from LX-2 cells that were embedded in matrigel for 72 hrs. FIG. 2B show results from primary HSCs that were treated with pro-fibrogenic factor TGFβ (5 ng/ml) or myosin inhibitors blebbistatin (Bleb) or BDM (2,3-Butanedione monoxime) for 48 hrs. Cells were harvested for protein and Western blots performed to detect Rev-erbα.

Figure 3A:
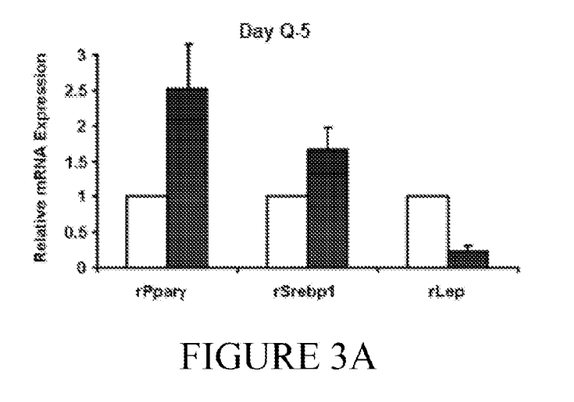
Figure 3B:
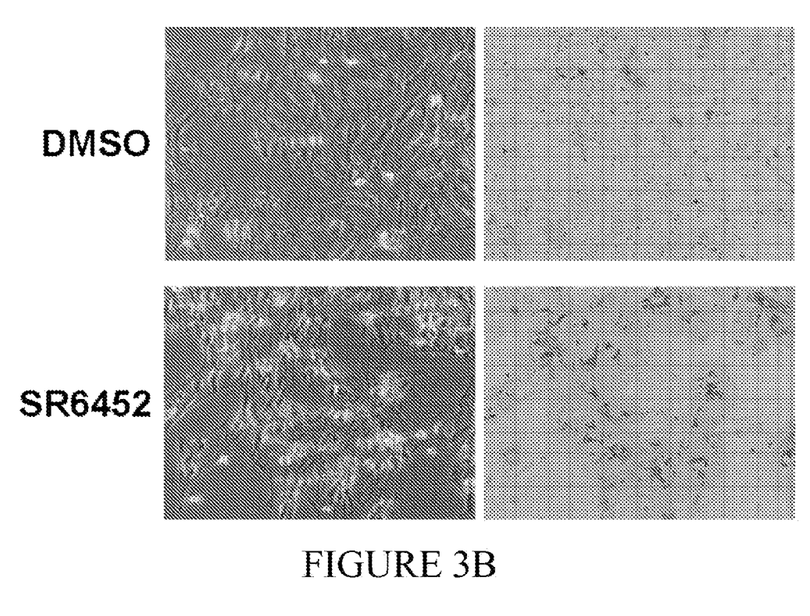

FIGS. 3A-B illustrates that modulation of Rev-erbα activity can regulate adipogenesis. Primary HSCs were culture-activated for 5 days (A) or 15 days (B). Cells were treated with vehicle (DMSO, open bar), or the Rev-erb modulator SR6452 (10 mM, purple bar) for the days indicated. The medium was changed every 48 hrs. FIG. 3A provides a chart summarizing the amount of PPARγ, SREBP1, and Lep mRNA on day 5. On day 15, cells were stained with Oil Red O as an indicator of adipogenesis and the results are shown in FIG. 3B.

Figure 4A:
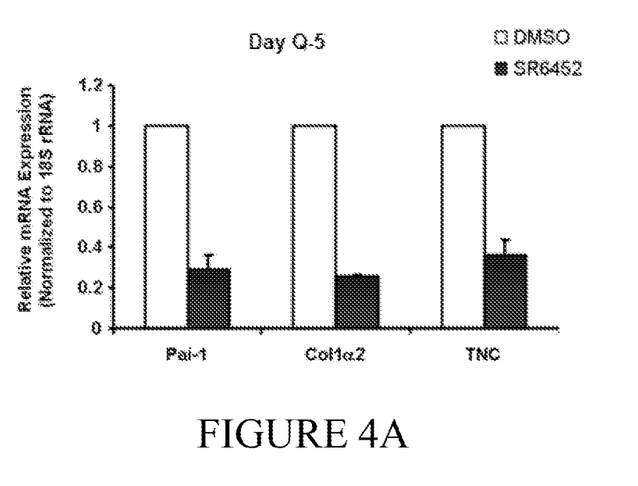
FIGS. 4A-B illustrate that the Rev-erb agonist SR6452 can suppress/decrease ECM gene expression. Primary rat HSCs were cultured with Rev-erb agonist SR6452 from quiescence (day Q) to day 5 (FIG. 4A) or from day 9 to day 12 (FIG. 4B) while being treated. qRT-PCR was performed to detect ECM gene expression. DMSO was used as the vehicle control.
Figure 4B:
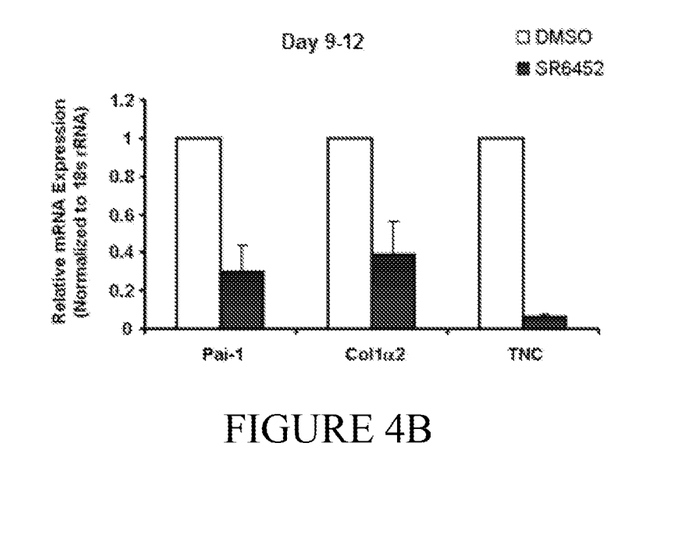

FIGS. 4A-B illustrate that the Rev-erb modulator SR6452 can suppress/decrease ECM gene expression. Primary rat HSCs were cultured from quiescence (day Q) to day 5 (FIG. 4A) or from day 9 to day 12 (FIG. 4B) and treated with Rev-erb modulator SR6452. qRT-PCR was performed to determine ECM gene expression. DMSO was used as the vehicle control, while SR6452 was used as the Rev-erb modulator.

Figure 5A:
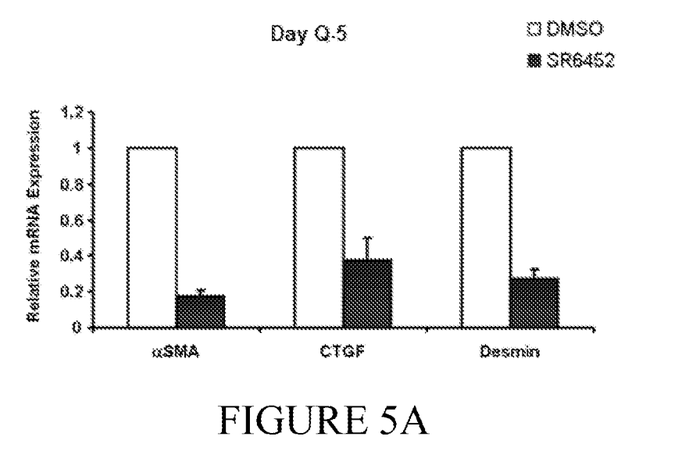
FIGS. 5A-D illustrate that Rev-erb agonist SR6452 can regulate myofibroblast marker expression and HSC contraction. Primary rat HSCs were cultured from quiescence (day Q) to day 5 (FIG. 5A) or from day 9 to day 12 (FIG. 5B) and treated with Rev-erb agonist SR6452. qRT-PCR was performed to detect myofibroblast gene expression. Samples were normalized with 18S rRNA.
Figure 5B:
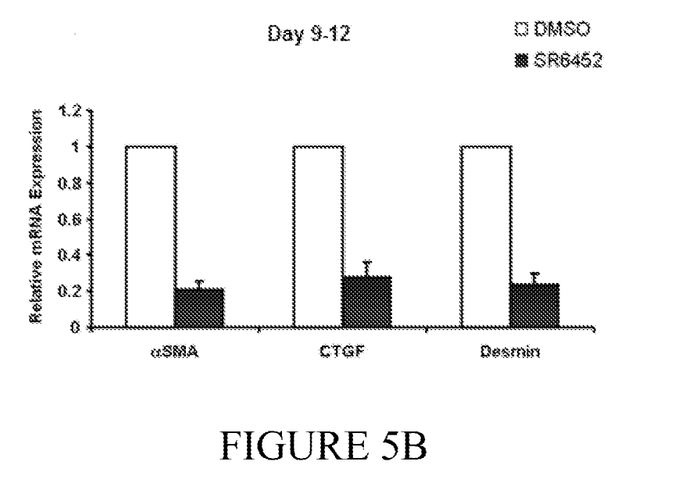
Figure 5C:
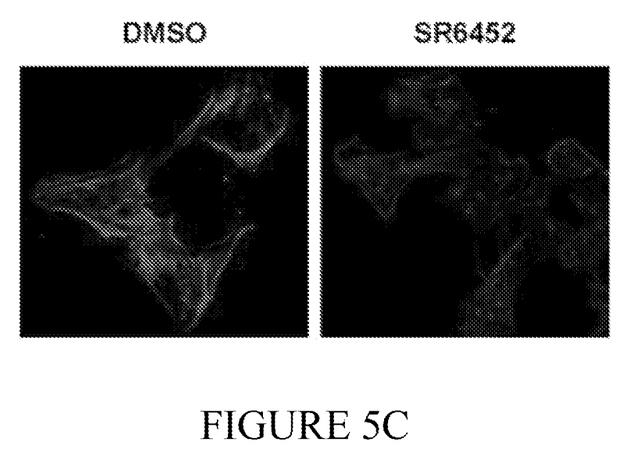
Figure 5D:
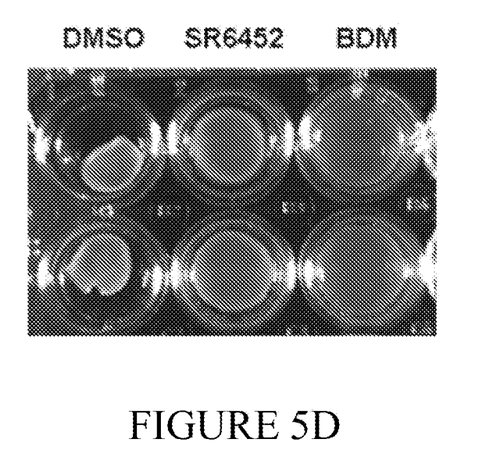

FIGS. 5A-D illustrate that Rev-erb modulator SR6452 can regulate myofibroblast marker expression and HSC contraction. Primary rat HSCs were cultured from quiescence (day Q) to day 5 (FIG. 5A) or from day 9 to day 12 (FIG. 5B) and treated with Rev-erb modulator SR6452. qRT-PCR was performed for myofibroblast gene expression. Samples were normalized with 18S rRNA. FIG. 5C shows results in which HSCs (day 9) were treated with DMSO or SR6452 for 72 hrs and immunocytochemistry was performed for αSMA (red fluorescence) and 4',6-diamidino-2-phenylindole (DAPI) (blue fluorescence). HSCs (day 5) were embedded in a collagen gel and treated as indicated for 48 hrs. Gels were then released from plastic surface and contraction monitored after 72 hrs. Materials used were DMSO (vehicle control), SR6452, Rev-erb modulator; and BDM (2,3-Butanedione monoxime), myosin inhibitor.

III. Brief Summary of Results

The results above show that during in vitro HSC activation, Rev-erbα protein expression is increased. The presence of Rev-erb modulator SR6452, in contrast, increased lipid content in activated HSCs and up-regulated expression of major adipogenic factors, notably PPARγ and SREBP1. SR6452 also significantly down-regulated expression of key extracellular matrix components, including Type I collagen, fibronectin, and tenascin C, concomitant with repressive effects on major regulatory and structural genes controlling myofibroblast contraction. Morphologically, SR6452-treated primary HSCs showed a slightly rounded/folded cytoplasm with disoriented actin fibers. Additionally, SR6452 impeded HSC contraction.

More specifically, the results shown in the figures and discussed above illustrate that expression of Rev-erbα mRNA and protein was modulated during HSC activation with peak protein expression on day 4. Regulation of Rev-erbα expression and subcellular localization was controlled by both pro- and anti-fibrotic factors. Matrigel or adipogenic mixture, MDIR, decreased Rev-erbα protein expression, while TGFβ increased expression and stabilized cytoplasmic Rev-erbα. Additionally, myosin inhibition decreased Rev-erbα protein expression. As can also be seen from the results above, exposure of quiescent HSCs to SR6452 promoted HSC adipogenesis.

These experiments illustrate that Rev-erbα expression during HSC activation inversely correlates with cellular adiposity. The data obtained with the Rev-erb specific modulator SR6452 indicates a suppressive effect of this compound on HSC activation, suggesting a functional role of Rev-erbα in maintaining/promoting the adipocyte phenotype while suppressing myofibroblast markers in HSCs.

Example 2: Studies Determining In Vivo Efficacy of Using REMAs as a Treatment for Portal Hypertension Studies were performed to determine the in vivo efficacy of using SR6452 as a treatment for portal hypertension. Rats underwent bile duct-ligation (~5 weeks, until ascites developed) to induce fibrosis and thus portal hypertension. Initial hemodynamic measurements were taken prior to addition of the agonist. SR6452 (10 μM/kg body weight) was administered via the femoral vein and measurements taken again one hour after administration.

I. Methods—Hemodynamic Measurements

Experiments were performed 5 weeks after male Sprague-Dawley rats underwent bile duct-ligation (BDL), when cirrhosis was fully established and ascites present. SR6452 (10 μM/kg body weight) was administered via the femoral vein and hemodynamic measurements taken one hour after administration. Hemodynamic studies were performed as previously described (J Hepatol 2012 57:1220-1227). Briefly, a laparotomy was performed under anesthesia. A PE-50 catheter was introduced into a small ileocolic vein and advanced to the portal vein for measurement of portal pressure. The left femoral artery and vein were cannulated with PE-50 catheters for measurement of mean arterial pressure, central venous pressure and blood withdrawal. Via the right carotid artery, another PE-50 catheter was advanced into the left ventricle under pulse curve control, for microsphere application. After insertion of all catheters, rats were allowed to stabilize hemodynamically for 30 min. Cardiac output and organ perfusions were measured using the colored microsphere method as described (J Hepatol 2012 57:1220-1227). Briefly, 300,000 systemic (yellow) microspheres (15 μm diameter) were injected in the left ventricle. The mesenteric portal-systemic shunt volume was estimated after injection of 150,000 blue microspheres in an ileocolic vein.

II. Results

The in vivo results, as shown in Tables 1-9, present hemodynamic measurements demonstrating that this agonist decreased portal pressure (PP) in cirrhotic rats by approximately 20% (23.7 vs. 19.1 mmHg; p=0.017) compared to baseline measurements (i.e., before SR6452 injection). See Table 1. This decrease in PP was a consequence of a significant drop in hepatic-portal vascular resistance [36% reduction (13.8 vs. 8.8 mmHg/min/100 g/ml; p=0.043)] (Table 4). Additionally, this agonist showed decreased splanchnic vascular resistance (13.5% reduction; 31.8 vs. 27.5 mmHg/min/100 g/ml; p=0.048) (Table 2). Besides increased portal hepatic resistance observed during cirrhosis, decreased splanchnic vascular resistance plays an important role in pathogenesis and maintenance of portal hypertension. Therefore, this data suggests that this agonist might have other side effects due to the decrease in splanchnic vascular resistance observed. However, studies will be further investigated to specifically target this agonist to the HSC to prevent systemic effects.

TABLE 1

| Study# | mean arterial pressure/ 30 (mmHg) | heart rate/ 30 (Hz) | portal pressure/ 30 (mmHg) | portal venous inflow (ml/min/g liver) |
|---|---|---|---|---|
| Before SR6452 (10 μM)_BDL ||||
| 1 | 91.97 | 138 | 32.45 | 0.1207063 |
| 2 | 129.2 | 123 | 9.432 | 0.405593 |
| 3 | 73.57 | 89 | 16.76 | 1.1151437 |
| 4 | 93.03 | 150 | 25.26 | 0.4346557 |
| 5 | 98.12 | 102 | 26.81 | 0.8550002 |
| 6 | 89.11 | 159 | 22.74 | 0.2397264 |
| 7 | 82.85 | 145 | 29.81 | 0.2807501 |
| 8 | 119.9 | 116 | 26.67 | 0.2419974 |
| means | 97.21875 | 127.75 | 23.7415 | 0.462 |
| SD | 18.57272535 | 24.49343935 | 7.439935157 | 0.345 |
| n | 8 | 8 | 8 | 8 |
| SEM | 6.566450019 | 8.659738531 | 2.630414301 | 0.121898244 |

TABLE 1-continued

| Study# | mean arterial pressure/ 30 (mmHg) | heart rate/ 30 (Hz) | portal pressure/ 30 (mmHg) | portal venous inflow (ml/min/g liver) |
|---|---|---|---|---|
| After SR6452 (10 μM)_BDL | | | | |
| 1 | 79.79 | 173 | 17.95 | 0.1349498 |
| 2 | 115 | 126 | 7.482 | 0.4605356 |
| 3 | 76.63 | 78 | 13.8 | 1.1731875 |
| 4 | 89.82 | 162 | 23.33 | 0.7779673 |
| 5 | 119.3 | 126 | 25.19 | 0.9090378 |
| 6 | 79.24 | 80 | 18.97 | 0.2682952 |
| 7 | 81.64 | 120 | 23.45 | 0.3209684 |
| 8 | 116.8 | 99 | 22.45 | 0.2778724 |
| means | 94.7775 | 120.5 | 19.07775 | 0.540 |
| SD | 18.8521865 | 34.73984949 | 5.970515215 | 0.369 |
| n | 8 | 8 | 8 | 8 |
| SEM | 6.665254456 | 12.28239158 | 2.110895898 | 0.130564176 |
| TTEST | 0.55728427 | 0.581348701 | 0.01758546 | 0.078307133 |

TABLE 2

| | Before SR6452 (10 μM)_BDL | | |
|---|---|---|---|
| Study# | portal venous inflow (ml/min/100 g k.g.) | splanchnic vascular resistance (mmHg*min*100 g/ml) | splanchnic vascular resistance without spleen (mmHg*min*100 g/ml) |
| 1 | 1.0578322 | 56.2660127 | 58.58735534 |
| 2 | 3.7140983 | 32.24685787 | 32.69124212 |
| 3 | 7.0671872 | 8.03855882 | 8.120482226 |
| 4 | 2.4412522 | 27.76034365 | 28.26840737 |
| 5 | 5.2072297 | 13.69442182 | 13.93688411 |
| 6 | 1.6824625 | 39.44813034 | 40.90707546 |
| 7 | 2.2280558 | 23.80550792 | 24.79055079 |
| 8 | 1.7458275 | 53.40161041 | 58.29932678 |
| means | 3.143 | 31.833 | 33.200 |
| SD | 2.602 | 17.306 | 18.629 |
| n | 8 | 8 | 8 |
| SEM | 0.7288592 | 6.118690863 | 6.586296855 |
| After SR6452 (10 μM)_BDL | | | |
| Study# | portal venous inflow (ml/min/100 g b.w.) | splanchnic vascular resistance (mmHg*min*100 g/ml) | splanchnic vascular resistance without spleen (mmHg*min*100 g/ml) |
| 1 | 1.1826584 | 52.2889788 | 57.89424206 |
| 2 | 4.2172186 | 25.4950028 | 25.83423239 |
| 3 | 7.4350378 | 8.450528658 | 8.553316465 |
| 4 | 4.3694684 | 15.21695408 | 15.39993391 |
| 5 | 5.5371564 | 16.99608846 | 17.40979587 |
| 6 | 1.8829664 | 32.00800609 | 33.05323291 |
| 7 | 2.5472318 | 22.84440701 | 23.66821059 |
| 8 | 2.004638 | 47.06585428 | 51.14824697 |
| means | 3.647 | 27.546 | 29.120 |
| SD | 2.133 | 15.434 | 17.393 |
| n | 8 | 8 | 8 |
| SEM | 0.754281452 | 5.456653552 | 6.149254941 |
| TTEST | 0.045349236 | 0.047716504 | 0.071093022 |

TABLE 3

| | Before SR6452 (10 μM)_BDL | | |
|---|---|---|---|
| Study# | mesenteric shunt flow (%) | shunt volume (ml/min/g liver) | shunt volume (ml/min/100 g k.g.) |
| 1 | 8.6270075 | 0.010413342 | 0.091259263 |
| 2 | 10.151558 | 0.041174009 | 0.377038843 |
| 3 | 24.693095 | 0.275363493 | 1.745107249 |
| 4 | 31.561646 | 0.137184493 | 0.770499377 |
| 5 | 11.542452 | 0.098687988 | 0.601041989 |
| 6 | 15.177738 | 0.036385045 | 0.25535975 |
| 7 | 27.947648 | 0.07846305 | 0.622689192 |
| 8 | 23.964379 | 0.057993174 | 0.418376719 |
| means | 19.208 | 0.092 | 0.610 |
| SD | 8.870 | 0.084 | 0.507 |
| n | 8 | 8 | 8 |
| SEM | 3.135862853 | 0.029695155 | 0.179300306 |
| After SR6452 (10 μM)_BDL | | | |
| Study# | mesenteric shunt flow (%) | shunt volume (ml/min/g liver) | shunt volume (ml/min/100 g b.w.) |
| 1 | 4.424613 | 0.005971006 | 0.052328057 |
| 2 | 2.206113895 | 0.01015994 | 0.093036646 |
| 3 | 10.966817 | 0.128661326 | 0.815386989 |
| 4 | 23.70114 | 0.184387119 | 1.035613823 |
| 5 | 10.371221 | 0.094278319 | 0.574270727 |
| 6 | 8.0342127 | 0.021555407 | 0.151281526 |
| 7 | 29.621504 | 0.095075667 | 0.75452837 |
| 8 | 40.058937 | 0.11131273 | 0.803036673 |
| means | 16.173 | 0.081 | 0.535 |
| SD | 13.460 | 0.064 | 0.383 |
| n | 8 | 8 | 8 |
| SEM | 4.758782262 | 0.02253318 | 0.135379972 |
| TTEST | 0.373723076 | 0.647281668 | 0.615551106 |

TABLE 4

| | Before SR6452 (10 μM)_BDL | | |
|---|---|---|---|
| Study# | hepatic portal venous flow (ml/min/100 g KG) | hepatic portal venous flow (ml/min/g liver) | hepatic portal-vascular resistance (mmHg*min*100 g/ml) |
| 1 | 0.966572937 | 0.110292958 | 32.53763767 |
| 2 | 3.337059457 | 0.364418991 | 2.526775477 |
| 3 | 5.322079951 | 0.839780207 | 2.961248261 |
| 4 | 1.670752823 | 0.297471207 | 14.52040043 |
| 5 | 4.606187711 | 0.756312212 | 5.603332217 |
| 6 | 1.42710275 | 0.203341355 | 15.23366135 |
| 7 | 1.605366608 | 0.20228705 | 17.9460566 |
| 8 | 1.327450781 | 0.184004226 | 19.33781679 |
| means | 2.533 | 0.370 | 13.833 |
| SD | 1.667 | 0.276 | 10.094 |
| n | 8 | 8 | 8 |
| SEM | 0.589455119 | 0.097574743 | 3.56889142 |
| After SR6452 (10 μM)_BDL | | | |
| Study# | hepatic portal venous flow (ml/min/100 g b.w.) | hepatic portal venous flow (ml/min/g liver) | hepatic portal-vascular resistance (mmHg*min*100 g/ml) |
| 1 | 1.130330343 | 0.128978794 | 14.9956162 |
| 2 | 4.124181954 | 0.45037566 | 1.571705631 |
| 3 | 6.619650811 | 1.044526174 | 1.933636738 |
| 4 | 3.333854577 | 0.593580181 | 6.69795262 |
| 5 | 4.962885673 | 0.814759481 | 4.874180385 |
| 6 | 1.731684874 | 0.246739793 | 10.37717674 |
| 7 | 1.79270343 | 0.225892733 | 12.52298602 |
| 8 | 1.201601327 | 0.16655967 | 17.8511787 |
| means | 3.112 | 0.459 | 8.863 |
| SD | 2.001 | 0.334 | 6.046 |
| n | 8 | 8 | 8 |
| SEM | 0.707429636 | 0.118126794 | 2.137509132 |
| TTEST | 0.033090553 | 0.050215568 | 0.043009894 |

TABLE 5

Before SR6452 (10 μM)_BDL

| Study# | hepatic portal-vascular resistance (mmHg*min*g Leber/ml) | portal sinusoidal resistance (10 3*dyne*s*cm −5) | mesenteric flow (ml/min/ 100 g KG) |
|---|---|---|---|
| 1 | 285.1496636 | 683.4037637 | 1.015918873 |
| 2 | 23.13820136 | 60.78367216 | 3.663611177 |
| 3 | 18.76681526 | 74.5359729 | 6.995889951 |
| 4 | 81.55411165 | 356.7889981 | 2.397375951 |
| 5 | 34.12611826 | 116.6830926 | 5.116638657 |
| 6 | 106.9138149 | 363.1767466 | 1.622457711 |
| 7 | 142.4213758 | 382.8652791 | 2.139524872 |
| 8 | 139.5076655 | 428.6110383 | 1.599160833 |
| means | 103.947 | 308.356 | 3.069 |
| SD | 88.439 | 213.383 | 2.062 |
| n | 8. | 8 | 8 |
| SEM | 31.26790019 | 75.4424056 | 0.728867856 |

After SR6452 (10 μM)_BDL

| Study# | hepatic portal-vascular resistance (mmHg*min*g liver/ml) | portal sinusoidal resistance (10 3*dyne*s*cm −5) | mesenteric flow (ml/min/ 100 g b.w.) |
|---|---|---|---|
| 1 | 131.4169526 | 323.2634427 | 1.068154583 |
| 2 | 14.39242964 | 39.01457997 | 4.161842256 |
| 3 | 12.25436023 | 49.34206305 | 7.345688688 |
| 4 | 37.61918055 | 165.1423232 | 4.317550996 |
| 5 | 29.6897435 | 101.767938 | 5.405577453 |
| 6 | 72.82976039 | 249.6786583 | 1.82342224 |
| 7 | 99.38345402 | 269.7072848 | 2.458572006 |
| 8 | 128.7826756 | 398.5791952 | 1.844638 |
| means | 65.796 | 199.562 | 3.553 |
| SD | 49.364 | 131.710 | 2.140 |
| n | 8 | 8 | 8 |
| SEM | 17.45281942 | 46.56635579 | 0.756565629 |
| TTEST | 0.065865538 | 0.036529214 | 0.054465327 |

TABLE 6

Before SR6452 (10 μM)_BDL

| Study# | % mesenteric flow of cardiac output (%) | hepatic arterial flow (ml/min/g liver) | hepatic arterial flow (ml/min/100 g KG) | % flow of cardiac output (%) |
|---|---|---|---|---|
| 1 | 1.949192005 | 0.139 | 1.2181528 | 2.337207982 |
| 2 | 4.357810368 | 0.8723744 | 7.988505 | 9.502206495 |
| 3 | 7.341683231 | 1.1204265 | 7.100666 | 7.451638157 |
| 4 | 4.619221486 | 0.5741987 | 3.2249979 | 6.213868786 |
| 5 | 11.74618608 | 1.0534371 | 6.4157754 | 14.72859366 |
| 6 | 3.26647415 | 0.4563633 | 3.2028772 | 6.448313268 |
| 7 | 7.124624949 | 0.5414934 | 4.2973365 | 14.31014486 |
| 8 | 3.402469858 | 0.2271056 | 1.6383945 | 3.485945745 |
| means | 5.476 | 0.623 | 4.386 | 8.060 |
| SD | 3.142 | 0.363 | 2.530 | 4.562 |
| n | 8 | 8 | 8 | 8 |
| SEM | 1.110970421 | 0.128360392 | 0.894503057 | 1.612797983 |

After SR6452 (10 μM)_BDL

| Study# | % mesenteric flow of cardiac output (%) | hepatic arterial flow (ml/min/g liver) | hepatic arterial flow (ml/min/100 g KG) | |
|---|---|---|---|---|
| 1 | 1.33586116 | 0.1773333 | 1.5540943 | 1.94358967 |
| 2 | 6.523263724 | 0.9036667 | 8.2750603 | 12.97031395 |
| 3 | 14.01848986 | 1.366 | 8.6569805 | 16.52095515 |
| 4 | 6.587657913 | 0.9228978 | 5.1834731 | 7.908869545 |
| 5 | 14.55851724 | 1.1176333 | 6.8077595 | 18.33492998 |
| 6 | 3.215912241 | 0.8093198 | 5.6800185 | 10.01766931 |
| 7 | 6.911925798 | 0.5347485 | 4.243808 | 11.93086309 |
| 8 | 3.541931644 | 0.3759295 | 2.7120456 | 5.207460829 |
| means | 7.087 | 0.776 | 5.389 | 10.604 |
| SD | 4.856 | 0.393 | 2.517 | 5.527 |
| n | 8 | 8 | 8 | 8 |
| SEM | 1.717012257 | 0.138902699 | 0.889752206 | 1.954255873 |
| TTEST | 0.100905023 | 0.020758014 | 0.017187987 | 0.070611074 |

TABLE 7

Before SR6452 (10 μM)_BDL

| Study# | renal arterial flow (ml/min/g kidney) | renal arterial flow (ml/min/ 100 g KG) | % renal flow of cardiac output (%) |
|---|---|---|---|
| 1 | 0.604035687 | 0.497125981 | 0.953810401 |
| 2 | 0.55422915 | 0.479935627 | 0.570876207 |
| 3 | 0.558904542 | 0.441235293 | 0.463044698 |
| 4 | 0.3045325 | 0.27630379 | 0.532377245 |
| 5 | 0.65625 | 0.483470395 | 1.109895305 |
| 6 | 0.722128 | 0.539483107 | 1.086134703 |
| 7 | 0.66575 | 0.51487698 | 1.714542058 |
| 8 | 0.25676 | 0.218444561 | 0.464775662 |
| means | 0.540 | 0.431 | 0.862 |
| SD | 0.170 | 0.118 | 0.44 |
| n | 8 | 8 | 8 |
| SEM | 0.060182335 | 0.041734466 | 0.155684104 |

After SR6452 (10 μM)_BDL

| Study# | renal arterial flow (ml/min/g kidney) | renal arterial flow (ml/min/ 100 g k.g.) | spleen arterial flow (ml/min/g spleen) |
|---|---|---|---|
| 1 | 0.4425 | 0.364180878 | 0.455453824 |
| 2 | 0.55475 | 0.480386657 | 0.752957143 |
| 3 | 0.655618478 | 0.517587512 | 0.987762427 |
| 4 | 0.359 | 0.324762625 | 0.495518195 |
| 5 | 0.73591475 | 0.542160754 | 1.460169012 |
| 6 | 0.66020743 | 0.493232854 | 0.86988334 |
| 7 | 0.569942201 | 0.440781253 | 1.239193852 |
| 8 | 0.37464 | 0.318733722 | 0.612007915 |
| means | 0.544 | 0.435 | 0.859 |
| SD | 0.150 | 0.088 | 0.357 |
| n | 8 | 8 | 8 |
| SEM | 0.04942395 | 0.031188532 | 0.126057552 |
| TTEST | 0.919439086 | 0.897405283 | 0.983583472 |

TABLE 8

Before SR6452 (10 μM)_BDL

| Study# | spleen arterial flow (ml/min/g spleen) | Spleen arterial flow (ml/min/ 100 g KG) | % spleen flow of cardiac output (%) |
|---|---|---|---|
| 1 | 0.164719376 | 0.041913327 | 0.080416975 |
| 2 | 0.187812099 | 0.050487123 | 0.060053674 |
| 3 | 0.240984703 | 0.071297249 | 0.074821334 |
| 4 | 0.148740484 | 0.043876249 | 0.084539979 |
| 5 | 0.361458261 | 0.090591043 | 0.207968418 |
| 6 | 0.210616811 | 0.060004789 | 0.120806904 |
| 7 | 0.3435 | 0.088530928 | 0.294808284 |
| 8 | 0.55 | 0.146666667 | 0.312056738 |
| means | 0.276 | 0.074 | 0.154 |
| SD | 0.136 | 0.035 | 0.103 |
| n | 8 | 8 | 8 |
| SEM | 0.0479568 | 0.012290852 | 0.03638978 |

After SR6452 (10 μM)_BDL

| Study# | renal arterial flow (ml/min/g kidney) | renal arterial flow (ml/min/ 100 g k.g.) | spleen arterial flow (ml/min/g spleen) |
|---|---|---|---|

TABLE 8-continued

| | | | |
|---|---|---|---|
| 1 | 0.45 | 0.114503817 | 0.143201372 |
| 2 | 0.206 | 0.055376344 | 0.086796778 |
| 3 | 0.302 | 0.089349112 | 0.170513573 |
| 4 | 0.176 | 0.051917404 | 0.079214837 |
| 5 | 0.525 | 0.131578947 | 0.35437368 |
| 6 | 0.209 | 0.05954416 | 0.105016154 |
| 7 | 0.344 | 0.088659794 | 0.24925441 |
| 8 | 0.6 | 0.16 | 0.307219662 |
| means | 0.352 | 0.094 | 0.187 |
| SD | 0.159 | 0.039 | 0.105 |
| n | 0.8 | 8 | 8 |
| SEM | 0.056115315 | 0.013815445 | 0.037059823 |
| TTEST | 0.06973027 | 0.062589528 | 0.1972608 |

TABLE 9

Before SR6452 (10 μM)_BDL

| Study# | cardiac output (ml/ min/100 g KG) | systemic vascular resistance (mmHg/ml/ min/100 g KG) | KG = body weight (g) | Liver (g) | Spleen (g) | Gastrointestinal (g) |
|---|---|---|---|---|---|---|
| 1 | 52.12 | 1.764581734 | 393 | 34.4413 | 1.90746 | 14.726 |
| 2 | 84.07 | 1.536814559 | 372 | 34.0648 | 3.13828 | 17.5192 |
| 3 | 95.29 | 0.772064225 | 338 | 21.42064 | 3.7044 | 13.497 |
| 4 | 51.9 | 1.792485549 | 339 | 19.04 | 3.0288 | 15.1862 |
| 5 | 43.56 | 2.252525253 | 399 | 24.304 | 2.6097 | 14.8652 |
| 6 | 49.67 | 1.794040668 | 351 | 24.6341 | 2.27344 | 15.4553 |
| 7 | 30.03 | 2.758907759 | 388 | 30.792 | 3.62295 | 17.44 |
| 8 | 47 | 2.55106383 | 375 | 27.0534 | 3.68503 | 17.8919 |
| means | 56.705 | 1.903 | 369.375 | 26.969 | 2.996 | 15.823 |
| SD | 21.745 | 0.625 | 24.101 | 5.695 | 0.681 | 1.597 |
| n | 8 | 8 | 8 | 8 | 8 | 8 |
| SEM | 7.687862187 | 0.220837898 | 8.520851525 | 2.013416693 | 0.240802901 | 0.564483214 |

After SR6452 (10 μM)_BDL

| Study# | cardiac output (ml/ min/100 g k.g.) | systemic vascular resistance (mmHg/ml/ min/100 g k.g.) | k.g. (8) | Liver (g) | Spleen (g) | Gastrointestinal (g) |
|---|---|---|---|---|---|---|
| 1 | 79.96 | 0.997873937 | 393 | 34.4413 | 1.90746 | 14.726 |
| 2 | 63.8 | 1.802507837 | 372 | 34.0648 | 3.13828 | 17.5192 |
| 3 | 52.4 | 1.46240458 | 338 | 21.42064 | 3.7044 | 13.497 |
| 4 | 65.54 | 1.370460787 | 339 | 19.04 | 3.0288 | 15.1862 |
| 5 | 37.13 | 3.213035281 | 399 | 24.304 | 2.6097 | 14.8652 |
| 6 | 56.7 | 1.397530864 | 351 | 24.6341 | 2.27344 | 15.4553 |
| 7 | 35.57 | 2.295192578 | 388 | 30.792 | 3.62295 | 17.44 |
| 8 | 52.08 | 2.242703533 | 375 | 27.0534 | 3.68503 | 17.8919 |
| means | 55.398 | 1.848 | 369.375 | 26.969 | 2.996 | 15.823 |
| SD | 14.761 | 0.709 | 24.101 | 5.695 | 0.681 | 1.597 |
| n | 8 | 8 | 8 | 8 | 8 | 8 |
| SEM | 5.218968409 | 0.250838828 | 8.520851525 | 2.013416693 | 0.240802901 | 0.564483214 |
| TTEST | 0.870445942 | 0.808342612 | | | | |

III. Brief Summary of the Results

As noted above, the present studies demonstrated a 20% decrease in portal pressure (PP) as a consequence of a significant drop (36% reduction) in hepatic-portal vascular resistance. A 20% decrease in PP is clinically relevant. This in vivo data supports the in vitro data suggesting that this decrease in hepatic-portal vascular resistance by SR6452 is due to this agonist acting directly on HSCs to inhibit contraction. Overall, the in vitro and in vivo data indicate that Rev-erb ligands (e.g., SR6452, SR9009, SR9011, etc.) or modulation of Rev-erb activity can be therapeutically effective, particularly as a vasodilator at the HSC level (i.e. reduction in HSC contraction).

Example 3: Specific Targeting of REMAs to HSCs

Rev-erbα is expressed in cell types other than HSCs, including hepatocytes. It is therefore desirable to limit the distribution of REMAs to activated HSCs. This can be done by linking the REMA to a suitable targeting moiety.

Accordingly, in this example, the REMA SR9009 is attached to mannose-6-phosphate human serum albumin (M6PHSA). The M6PHSA moiety binds to the insulin-like growth factor II receptor on activated HSCs, and has been shown to successfully target, e.g., a Rho kinase inhibitor and an ALK5 inhibitor to HSCs. See, e.g., van Beuge et al. (2013), PLOS ONE 8(2): e56442. The linkage between SR9009 and M6PHSA can be achieved using the Universal Linkage System (ULS™), as described. Id.

Many modifications and other embodiments of the invention set forth herein will come to mind to one skilled in the art to which these inventions pertain having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating portal hypertension in a mammal in need thereof, the method comprising:
   detecting portal hypertension in the mammal;
   providing a composition comprising a therapeutically effective amount of one or more Rev-erb-modulating agents (REMAs), wherein the one or more REMAs is selected from the group consisting of 1,1-Dimethyl-ethyl N-[(4-chlorophenyl)methyl]-N-[(5-nitro-2-thienyl)methyl])glycinate; N-Benzyl-N-(4-chlorobenzyl)-1-(5-nitrothiophen-2-yl)methanamine; N-Benzyl-N-(3,4-dichlorobenzyl)-1-(5-nitrothiophen-2-yl)methanamine; 2-((4-chlorobenzyl)((5-nitrothiophen-2-yl)methyl)amino)-N,N-dimethylacetamide; SR9009; SR9011; and combinations thereof, wherein the one or more REMAs is linked to a carrier/targeting moiety that selectively targets hepatic stellate cells (HSCs), and wherein the carrier/targeting moiety is mannose-6-phosphate modified human serum albumin; and administering the composition to the mammal, said therapeutically effective amount comprising a quantity sufficient to modulate at least one of Rev-erbα expression, activity, and subcellular localization in at least a portion of the mammal's HSCs for treating and/or ameliorating the portal hypertension detected in the mammal.

2. The method of claim 1, wherein the therapeutically effective amount of the one or more REMAs comprises an amount sufficient to halt activation of HSCs, revert at least a portion of any activated HSCs into a quiescent phenotype, or a combination thereof.

3. The method of claim 1, wherein the mammal's HSCs exhibit an initial degree of contractility prior to administration of the one or more REMAs, and a second degree of contractility subsequent to administration of the one or more REMAs that is less than the initial degree of contractility, and wherein i) the second degree of contractility subsequent to administration of the one or more REMAs is sufficiently reduced in comparison to the initial degree of contractility such that at least a portion of the mammal's liver sinusoids are at least partially relaxed; and/or ii) the second degree of contractility subsequent to administration of the one or more REMAs is exhibited at least once from between 0.15-24 hours from a time of administration.

4. The method of claim 1, wherein the one or more REMAs modulates Rev-erbα isoform activity or subcellular localization in at least a portion of the mammal's HSCs, increases Rev-erbα isoform nuclear activity and/or nuclear localization, decreases Rev-erbα isoform cytoplasmic activity and/or cytoplasmic localization, or a combination thereof.

5. The method of claim 1, wherein the one or more REMA modulates expression, activity, and/or subcellular localization of at least one Rev-erb in addition to Rev-erbα in at least a portion of the mammal's HSCs.

6. The method of claim 5, wherein the at least one Rev-erb in addition to Rev-erbα is Rev-erbβ.

7. The method of claim 1, wherein the mammal also suffers from at least one of viral hepatitis, autoimmune hepatitis, hepatic cirrhosis, acute alcoholic hepatitis, schistosomiasis, primary biliary cirrhosis, idiopathic portal hypertension, acute and fulminant hepatitis, congenital hepatic fibrosis, peliosis hepatitis, veno-occlusive disease, Budd-Chiari syndrome, vitamin A toxicity, Sclerosing cholangitis, non-alcoholic steatophepatitis (NASH), non-alcoholic fatty liver disease (NAFLD), alcoholic liver disease, a metabolic liver disease, Wilson's disease, and hemochromatosis.

8. The method of claim 1, wherein Rev-erbα expression is modulated by at least 10%, 15%, 20%, 25%, 30%, 35%, 40%, 45%, 50%, 55%, 60%, 65%, 70%, 75%, 80%, 85%, 90%, 95%, or more, and/or Rev-erbα nuclear localization is increased to at least 10%, 15%, 20%, 25%, 30%, 35%, 40%, 45%, 50%, 55%, 60%, 65%, 70%, 75%, 80%, 85%, 90%, 95%, or more.

9. The method of claim 1, further comprising the step of perfusing the composition comprising one or more REMA through a targeted tissue of the mammal.

10. The method of claim 9, wherein the targeted tissue comprises a hepatic stellate cell.

11. The method of claim 1, wherein the one or more REMAs is administered in combination with miR-19b.

12. The method of claim 1, further comprising administering a non-REMA therapeutic agent either at the same time or at a different time as administering the composition comprising the one or more REMA, wherein the non-REMA therapeutic agent is an anti-viral agent, miR-19b, an angiotensin II receptor antagonist, or a vasodilating medicament.

13. The method of claim 1, wherein the therapeutically effective amount of the one or more REMAs comprises an amount sufficient to reduce portal hypertension in the mammal by 5-30%.

14. The method of claim 1, wherein the therapeutically effective amount of the one or more REMAs comprises an amount sufficient to reduce the hepatic-portal vascular resistance in the mammal by 7.7-53%.

15. A pharmaceutical composition for treating portal hypertension in a mammal, the composition comprising:

a therapeutically effective amount of one or more Rev-erb-modulating agents (REMAs), the one or more REMAs being selected from the group consisting of 1,1-Dimethylethyl N-[(4-chlorophenyl)methyl]-N-[(5-nitro-2-thienyl)methyl])glycinate, N-Benzyl-N-(4-chlorobenzyl)-1-(5-nitrothiophen-2-yl)methanamine, N-Benzyl-N-(3,4-dichlorobenzyl)-1-(5-nitrothiophen-2-yl)methanamine; 2-((4-chlorobenzyl)((5-nitrothiophen-2-yl)methyl)amino)-N,N-dimethylacetamide, SR9009, SR9011, and combinations thereof, and the one or more REMAs being linked to a carrier/targeting moiety that selectively targets hepatic stellate cells (HSCs), wherein the carrier/targeting moiety is mannose-6-phosphate modified human serum albumin; and wherein the therapeutically effective amount of the one or more REMAs is a quantity sufficient to modulate at least one of Rev-erbα expression, activity, and subcellular localization in at least a portion of the mammal's HSCs for treating and/or ameliorating portal hypertension in the mammal.

16. The pharmaceutical composition of claim 15, wherein the one or more REMA comprises SR9009 or SR9011.

17. The pharmaceutical composition of claim 15, wherein the composition is provided in a form selected from a liquid injectable composition, loaded nanoparticles, tablet, a capsule, an orally administrable liquid, and a transdermal patch.

* * * * *